(12) United States Patent
Lepore et al.

(10) Patent No.: US 6,203,484 B1
(45) Date of Patent: Mar. 20, 2001

(54) METHODS FOR DISINFECTING WASTES

(75) Inventors: Anthony Lepore, Canton, MI (US); Siegfried Lang, Ludwigshafen (DE)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 08/826,093

(22) Filed: Mar. 24, 1997

(51) Int. Cl.$^7$ .................................................. B09B 3/00
(52) U.S. Cl. .................. 588/255; 588/258; 588/901; 422/28; 422/37
(58) Field of Search .................. 588/252, 255, 588/258, 901; 422/28, 37

(56) References Cited

U.S. PATENT DOCUMENTS

| | | | |
|---|---|---|---|
| 3,911,107 | * 10/1975 | Krezanoski | 422/37 |
| 4,113,857 | 9/1978 | Shetty . | |
| 4,171,226 | 10/1979 | Hesselgren . | |
| 4,271,149 | 6/1981 | Wimicov et al. . | |
| 4,526,751 | * 7/1985 | Gartner | 422/37 |
| 4,816,307 | 3/1989 | Honeycutt . | |
| 4,900,500 | 2/1990 | Honeycut . | |
| 5,091,443 | 2/1992 | Karakelle et al. . | |
| 5,236,703 | 8/1993 | Usala . | |
| 5,252,340 | 10/1993 | Honeycutt | 424/489 |
| 5,287,960 | 2/1994 | Kalb et al. | 206/210 |
| 5,370,869 | * 12/1994 | Shanbrom | 422/28 |
| 5,417,977 | * 5/1995 | Honeycutt | 424/443 |
| 5,481,064 | * 1/1996 | Kato et al. | 588/255 X |
| 5,591,350 | * 1/1997 | Piechocki et al. | 422/28 X |
| 5,595,731 | 1/1997 | Vallieres . | |
| 5,635,196 | * 6/1997 | Murphy | 424/409 |
| 5,639,481 | 6/1997 | Kessler et al. . | |
| 5,674,175 | * 10/1997 | Bailey | 588/255 |
| 5,684,042 | 11/1997 | Greff et al. . | |

FOREIGN PATENT DOCUMENTS

| | | |
|---|---|---|
| 0 120 301 A2 | 10/1984 | (EP) . |
| 0 440 962 | 8/1991 | (EP) . |
| WO 95 15771 | 6/1995 | (WO) . |
| WO 97 34476 | 9/1997 | (WO) . |

OTHER PUBLICATIONS

International Search Report for PCT/US 98/05556 dated Jul. 13, 1998.

* cited by examiner

Primary Examiner—George Suchfield
(74) Attorney, Agent, or Firm—Nixon & Vanderhye P.C.

(57) ABSTRACT

The invention provided relates to the use of polyvinylpyrrolidone-iodine complexes in combination with gelling agents to produce strong disinfectants which not only physically stabilize biohazardous and infectious wastes but also kill pathogens contained in the wastes. The gelling agents include polyacyrlates that are superabsorbents.

13 Claims, No Drawings

METHODS FOR DISINFECTING WASTES

FIELD OF THE INVENTION

The invention relates to the fields of wastes treatment and disposal. In particular, the invention relates to the use of iodine complexes in combination with gelling agents to produce strong disinfectants which not only physically stabilize biohazardous and infectious wastes but also kill pathogens contained in the wastes.

BACKGROUND OF THE INVENTION

Wastes, particularly infectious human wastes, present a vast array of health problems for humans. For example, wastes may contain viral, bacterial, and fungal contaminants that may be spread to human and animal populations through such pests as mosquitoes and flies. One area of concern to humans is the spread of infectious diseases when such diseases are generated in medical environments such as hospitals and clinics. Blood borne pathogens such as hepatitis B and HIV viruses may be found in blood, urine, and other bodily fluids found in medical environments. Theses fluids, although ultimately disposed of, present dangers not only to those who may come into direct contact with the wastes during generation of the waste, such as hospital personnel and patients, but also workers involved with the disposal of the waste.

Various methods have been devised to treat medical wastes including the use of disinfectants and antimicrobial agents. However, even with the use of these agents, prior to and even after treatment, workers may still be exposed when wastes spill, leak or aerosolize from their containers. Accordingly, in order to prevent such mishaps workers have developed methods to contain the wastes by using solidifying and gelling agents.

One problem encountered by workers who handle contaminated liquid wastes is that these wastes are generally treated and disposed of using disinfectants. For example, phenol has been used in combination with gelling agents. Specifically ortho-benzyl-para-chlorophenol is used in combination with a gelling agent such as starch grafted polyacrylate. This composition is poured into canisters containing liquid wastes and the liquid turns into a highly viscous gelatin-like substance. Of course, many of these agents pose general questions and concerns regarding their toxicity and potential of environmental harm.

Iodine has been used as a biocide for many years. Iodine has several properties that make it difficult to use alone as a biocide. For example, iodine is insoluble in water. Also, when placed in volatile solutions such as in alcohols, the concentration of the iodine varies due to evaporation of the alcohol. High concentrations of iodine can lead to severe irritation of the skin.

In an effort to overcome these problems, workers developed an anti-microbial composition comprising polyvinyl pyrrolidone polymer, in combination with iodine ("PVP-I). Polyvinyl pyrrolidone and iodine, when combined in an aqueous solution, form a complex. The major complex formed is a triiodide. Some of the iodine reacts with water and is reduced to iodide. Some of the iodine also becomes covalently linked to the carbon atoms of the polyvinyl pyrrilidone. It is generally accepted that the antimicrobial activity of PVP-I arises from the release of elemental iodine (free iodine) in solution. In solution, the triiodide species is in equilibrium with iodine and Iodide. Accordingly, pH, concentration, and temperature play an important role in antimicrobial properties of any PVP-I solution.

PVP-I solutions have been used in the medical industry as a disinfectant and is provided in topical cleaners. It is also used as a scrub and with swabs. Crosspovidone-iodine has also been impregnated onto cellulose filters.

One noted drawback to the use of PVP-I is that it is known to be unstable at low pH. Heretofore, attempts to combine gelling agents with disinfecting agents have not produced a superior product having good gelling properties while maintaining an effective disinfectant qualities.

Accordingly, it is an object of the present invention to not only provide a composition that disinfects wastes which contain a high organic (e.g., proteins) load but one that also provides adequate gelling or solidifying properties.

SUMMARY OF THE INVENTION

Provided herein is a composition comprising: (a) polyvinylpyrrolidone; (b) iodine; and (c) a gelling agent.

Also provided by the present invention is a composition comprising: (a) polyvinylpyrrolidone; (b) iodine; and a (c) gelling agent; wherein the composition is provided in an amount that is effective in killing a pathogen in a liquid waste containing blood and the composition contains sufficient quantity of polyvinylpyrrolidone and iodine such that when a sufficient amount of the composition is added to 90 grams of a liquid waste containing blood the weight of the combined weight of the polyvinylpyrrolidone and the iodine composition is greater than 0.3% of the total weight of the waste containing the composition. The upper concentration of the composition in the waste is the saturation level of the gelling agent preferably, the total weight of the composition in solution is no more than 10% of the total weight of the solution containing the composition.

Further provided herein is a composition comprising: (a) polyvinylpyrrolidone, (b) iodine; and (c) a gelling agent and the composition is provided in an amount that is effective in killing a pathogen in a liquid waste containing blood and wherein the weight of the composition is such that when added to a liquid waste containing blood, is less than or equal to 10%, by weight, of the total weight of the waste containing the composition and the amount of the combined weight of polyvinylpyrrolidone and iodine is such that when the composition is added to a liquid waste containing blood, is greater than 0.3% of the total weight of the waste containing the composition.

The pathogens that are killed by the present invention include bacterial and viruses that are hazardous to animals including humans.

The composition surprisingly provides a 6 log kill (microbial) in 24 hours, preferably in about 8 hours, most preferably in about 4–6 hours.

In one aspect of the invention, the concentration, in a liquid waste, of the composition is in the range, by weight, of 0.3% up to about 10%, preferably from 0.3% to about 5%, most preferably at about 4% The composition provides superior and unexpected gelling and solidifying properties at low pH. Preferably, the pH of the solution containing the composition is less than 6, preferably less than or equal to about 4.

A further embodiment of the invention is provided comprising a method of treating liquid waste comprising: adding polyvinyl pyrrolidone, iodine, and a gelling agent to an aqueous waste stream such that the concentration of the combined weight of the polyvinylpyrrolidone and iodine is greater than 0.3%, by weight, of the total weight of the waste, polyvinylpyrrolidone, iodine and gelling agent.

The methods may be modified by addition of elements of compositions described herein.

The wastes streams best treated using embodiments of the present invention include animal wastes, preferably liquid human medical wastes generated for example during surgery.

Another embodiment of the present invention is provided herein comprising a system for treating liquid waste stream having: (a) an aqueous waste comprising human liquid waste; (b) a polyvinylpyrrolidone and iodine complex wherein the concentration of the complex is, by weight of the total weigh of the system, greater than 0.3%; and (c) a gelling agent.

DETAILED DESCRIPTION OF THE INVENTION

The gelling agent used in the present invention comprises a superabsorbent composition. Preferably, the gelling agents of the preferred present invention comprise acrylate polymers based on the terpolymer of acrylic acid, sodium acrylate and a cross-linker. These gelling agents are superabsorbents and include crosslinked polymers of acrylate or methacrylate monomers and a crosslinking agent such as crosslinkers including di- and tri acrylate esters such as 1,1,1-trimethylolpanetriacrylate, N,N'-methylenebisacrylamide, triallyamine, ethyleneglycoldiacrylate, tetraerthlyeneglycoldicacyrlate, trimethylolpropanetriacrylate and the methylate of any of the above mentioned acrylates. These polymers include hydrophilic esters of acrylic or methacrylic acid (e.g., 2-hydroxyethylmethacrylate and its analogs). A preferred example is an hydroxyethyl(meth)acrylate hydrogel.

The super absorbents also include ionogenic monomers such as acrylic and methacrylic acid (or their sodium salts) and a cross linker. One example includes poly(acrylic acid) hydrogels.

Other polymerization additives may be employed in the invention. These include mercapto compounds, formic acid, carbon tetrachloride, isopropanol, monobasic sodium phosphate and hypophosphite salts.

Examples of superabsorbent polymers that may be used in the present invention include Stockhausen's AP® acrylate series (e.g., AP® 75, AP® 80, AP® 80 HS AP® 80 HSB, AP® 85, AP® 85-13, AP® 85-38). The chemical basis for the series being the sodium salt of crosslinked polyacrylic acid, in some cases containing a polyalcohol.

Other superabsorbent materials that may be used in the present invention include polyacrylic acid polymers such as those represented by Carbopol® Resins (e.g., Types, 907, 910, 941, 934, 934P and 940, having approximate molecular weights of 450,000, 750,000, 1,250,000, 3,000,000, 3,000,000 and 4,000,000 respectively).

Another embodiment of the present invention includes Medi-Gel® 100 superabsorbent polymer comprising: potassium polyacrylate, lightly crosslinked (92% to 98%); water (2% to 8%); hydrophobic silicon dioxide, amorphous (0% to 3%) and acrylic acid (<0.08%).

Preferably the gelling agents are provided in a dry composition such that the weight of the gelling agent is greater than about 65% of the total weight of the composition.

In the present invention, a polyvinylpyrrolidone is complexed with iodine. Preferred complexes include PVP-I 30/06, PVP-I FC 1026. PVP-I 30/06 means that the K value of the PVP is 30 and 06 is loss of iodine in % during storage conditions of a 10% PVP-I solution held for 15 hours at 80° C. The 30/06 product comprises an iodine content between 9.0% and 12.0% (on a dry basis). The nitrogen content is not less than 9.5% and not more than 11.5% (on a dry basis).

The PVP-I FC 1026 differs from the 30/06 product in that 16–18% free iodine is available (on a dry basis) and the nitrogen content is 8.5 to 9.6% (on a dry basis).

Preferred compositions of the present invention comprise a combination of ingredients such that the concentration, by weight, of the polyvinyl pyrrilidone and iodine, in a aqueous solution containing ten percent or less, by weight, of the composition is from about 0.4 to 0.5% to about 0.7 to 0.8%, most preferably about 0.5% to about 0.7%.

In another embodiment of the invention, the gelling composition comprises a combination of ingredients such that the concentration, by weight, of the polyvinyl pyrrilidone and iodine, in a aqueous solution containing ten percent or less, by weight, of the composition is greater than 0.3% to about 1%.

Acids may also be included in the invention in amounts up to 10% of the total weight of the composition, preferably less than 1%. Preferred acids are those that can be provided in powder form at room temperatures such as citric, boric, and phosphoric acids.

Iodate salts may also be used in the invention. The preferred amount of iodate salt used is less then 0.5%. Potassium iodate is the preferred iodate salt used in the present invention.

It is preferred that the PVP-iodine, potassium iodate and acrylic polymer, be mixed in a large batch format.

Initial work performed on polyacrylates in solution (e.g., 20–24 grams PVP-I (1.9%) and 40 grams of potassium polyacrylate in 1200 milliliters 0.9% NaCI did not achieve a $1 \times 10^6$ kill (e.g., *Bacillus subtillis*) within 24 hours. The pH of the solution was between 5–6, that is, a buffered aqueous solution containing PVP-I 30/06, saline solution and a buffer had a pH of about 5–6 prior to the addition of the gelling agent. It was concluded that when using potassium polyacrylate the formulations would be unstable or that poor gelling would occur at low pH. A low pH is desirable in order to achieve a preferable free iodine concentration of about 0.2% in solution. Accordingly, aqueous solutions of PVP-I and potassium polyacrylate having a combined concentration in solution of about 5.1% (1.9% PVP-I) was not effective in solutions having a pH at about and having free iodine concentrations at about were not effective in killing microbes.

The most preferred use of the present invention is in hospital room canisters used to capture bodily fluids suctioned during surgery.

The following examples are illustrative only and are not meant to limit the invention in any manner.

EXAMPLE 1

*Bacillus subtillis* was grown at 37° C. for 3 days on Antibiotic Medium No. 1 (Difco) agar and supplemented with 100 mg/L of Manganese sulfate to enhance sporilation. Spores were flushed from the agar surface with sterile distilled water. The organism was heated at 56° C. for 30 minutes and then washed three more times. After the third washing, the bacterial suspension was brought up to volume with saline to provide sufficient quantities for testing. It was then heated at 65° C. for 30 minutes. The concentration of the suspension was approximately $1 \times 10^8$ (colony forming units (CFU/g)) as determined by a plate-counting methodology.

For each sample tested, 100 mls of sterile distilled water was placed into a specimen container. Ten milliliters of the spore inoculated suspension was then added and mixed to provide a homogenous solution. Four compositions were prepared as displayed in Table 1.

TABLE 1

| Sample # | Quantity |
|---|---|
| 1 (control) | 4.0 grams Dynasorb ® Hydrosafe 85 acrylate superabsorbent polymer (Stockhausen) |
| 2 | 4.0 grams Dynasorb ® Hydrosafe 85 acrylate superabsorbent polymer (4.0 g) 1.0 gram PVP-I 30/06 (Total weight in solution = 4.3%; PVP-I = 0.87%) |
| 3 | 4.0 grams Dynasorb ® Hydrosafe 85 acrylate superabsorbent polymer (4.0 g) 1.0 gram PVP-I 30/06 0.150 grams citric acid 0.200 grams potassium iodate (Total weight in solution = 4.6%; PVP-I = 0.87%) |

For each formulation, the ingredients were mixed with a spatula and then poured into specimen containers. The pH of the mixtures was in the range of about 2.9 to about 3.2. The testing products were allowed to react 5 minutes; gelling occurred within 1 minute. After predetermined time intervals (0, 2, 4 and 24 hours), grab samples from each blend were drawn. Two samples from each mixture were weighed into empty agar plates to which Antibiotic Medium No. 1 (Difco) was added. Another 1 g sample was transferred to a 9 ml Neutralizer Broth (Difco) to neutralize the effect of active ingredients. The Neutralizer Broth-Tubes were serially diluted in Phosphate Buffer Saline (PBS) and plated in duplicate on Antibiotic Medium No. 1. The plates were incubated at 37° C. for 48 hours and the colonies were counted.

The results are displayed in Tables 2–6.

TABLE 2

Sample #0 (CFU/g)

| Time (hours) | 0 | 2 | 4 | 24 |
|---|---|---|---|---|
| | $>10^3$ | $>10^3$ | $>10^3$ | $69 \times 10^3$ |
| | $>10^3$ | $>10^3$ | $>10^3$ | $86 \times 10^3$ |
| | $240 \times 10^4$ | $163 \times 10^4$ | $86 \times 10^4$ | $5 \times 10^4$ |
| | $252 \times 10^4$ | $179 \times 10^4$ | $89 \times 10^4$ | $9 \times 10^4$ |
| | $25 \times 10^5$ | $12 \times 10^5$ | $7 \times 10^5$ | $2 \times 10^5$ |
| | $18 \times 10^5$ | $6 \times 10^5$ | $5 \times 10^5$ | 0 |
| | $4 \times 10^5$ | $1 \times 10^6$ | $1 \times 10^6$ | $1 \times 10^6$ |
| | $2 \times 10^6$ | $1 \times 10^6$ | $1 \times 10^6$ | 0 |
| Average | | | | $1 \times 10^5$ |

TABLE 3

Sample #1 (CFU/g)

| Time (hours) | 0 | 2 | 4 | 24 |
|---|---|---|---|---|
| | 185 | 73 | 26 | 0 |
| | 145 | 55 | 13 | 0 |
| | $80 \times 10^3$ | $7 \times 10^3$ | $1 \times 10^3$ | 0 |
| | $73 \times 10^3$ | $5 \times 10^3$ | 0 | 0 |
| | $8 \times 10^4$ | $1 \times 10^4$ | 0 | 0 |
| | $9 \times 10^4$ | 0 | 0 | 0 |
| | $3 \times 10^5$ | 0 | 0 | 0 |
| Average | | | | $1 \times 10^1$ |

TABLE 4

Sample #2 (CFU/g)

| Time (hours) | 0 | 2 | 4 | 24 |
|---|---|---|---|---|
| | 110 | 52 | 4 | 0 |
| | 100 | 41 | 2 | 0 |
| | $78 \times 10^3$ | $4 \times 10^3$ | 0 | 0 |
| | $70 \times 10^3$ | $2 \times 10^3$ | 0 | 0 |
| | $7 \times 10^4$ | 0 | 0 | 0 |
| | $4 \times 10^4$ | 0 | 0 | 0 |
| | $3 \times 10^5$ | 0 | 0 | 0 |
| | $1 \times 10^5$ | 0 | 0 | 0 |

TABLE 5

Sample #3 (CFU/g)

| Time (hours) | 0 | 2 | 4 | 24 |
|---|---|---|---|---|
| | unable to count | unable to count | unable to count | 0 |
| | unable to count | unable to count | unable to count | 0 |
| | $19 \times 10^3$ | 0 | 0 | 0 |
| | $37 \times 10^3$ | 0 | 0 | 0 |
| | $1 \times 10^4$ | 0 | 0 | 0 |
| | $1 \times 10^4$ | 0 | 0 | 0 |
| | $1 \times 10^5$ | 0 | 0 | 0 |
| | 0 | 0 | 0 | 0 |

TABLE 6

Sample #4 (CFU/g)

| Time (hours) | 0 | 2 | 4 | 24 |
|---|---|---|---|---|
| | unable to count | unable to count | unable to count | 0 |
| | unable to count | unable to count | unable to count | 0 |
| | $44 \times 10^3$ | 0 | 0 | 0 |
| | $41 \times 10^3$ | 0 | 0 | 0 |
| | $3 \times 10^4$ | 0 | 0 | 0 |
| | 0 | 0 | 0 | 0 |
| | $1 \times 10^5$ | 0 | 0 | 0 |
| | 0 | 0 | 0 | 0 |
| | $1 \times 10^6$ | 0 | 0 | 0 |

Sample #4 is a replicate of Sample #3. Surprisingly, the average CFU/g for both Samples #3 and #4 was 0 after four hours (for those samples that could be counted).

The results indicate that both samples were effective in achieving a 6 log kill of *Bacillus subtilis* within 24 hours and that a 6 log kill may be obtained by four hours.

EXAMPLE 2

Samples containing the ingredients listed in Table 7 were prepared (dry mix).

TABLE 7

| Sample # | Quantity |
|---|---|
| 1 (control) | 4.0 grams Dynasorb ® Hydrosafe 85 acrylate superabsorbent polymer (Stockhausen) 0.5 g PVP-I 30/06 |

TABLE 7-continued

| Sample # | Quantity |
|---|---|
| | 0.150 g citric acid |
| | 0.200 potassium iodate |
| | (Total percent by weight of the composition in solution = 4.2%; weight of the PVP-I in solution = 0.44%) |
| 2 | 4.0 grams Dynasorb ® Hydrosafe 85 acrylate superabsorbent polymer (4.0 g) |
| | 0.5 gram PVP-I 30/06 |
| | (Total percent by weight of the composition in solution = 3.9%; the percent by weight of the PVP-I in solution = 0.44%) |
| 3 | 4.0 grams Dynasorb ® Hydrosafe 85 acrylate superabsorbent polymer (4.0 g) |
| | 0.75 gram PVP-I 30/06 |
| | 0.150 grams citric acid |
| | 0.200 grams potassium iodate |
| | (Total percent by weight of the composition in solution = 4.4%; weight of the PVP-I in solution = 0.65%) |
| 4 | 4.0 grams Dynasorb ® Hydrosafe 85 acrylate superabsorbent polymer (4.0 g) |
| | 0.75 gram PVP-I 30/06 |
| | (Total percent by weight of the composition in solution = 4.1%; the percent by weight of the PVP-I in solution = 0.65%) |
| 5 | 4.0 grams Dynasorb ® Hydrosafe 85 acrylate superabsorbent polymer (4.0 g) |
| | 0.5 grams PVP-I FC1026 |
| | (Total percent by weight of the composition in solution = 3.9%; the percent by weight of the PVP-I in solution = 0.44%) |
| 6 | 4.0 grams Dynasorb ® Hydrosafe 85 acrylate superabsorbent polymer (4.0 g) |
| | 0.75 grams PVP-I FC1026 |
| | (Total percent by weight of the composition in solution = 4.1%; the percent by weight of the PVP-I in solution = 0.65%) |

The compositions were tested according to the procedures set forth in Example 1. The pH of the mixtures were about 3.1 and the theoretical level of free iodine is about 9–10 ppm. Gelling took place within one minute in all samples. The results are listed in Table 8 below.

TABLE 8

| | (CFU/g) | | | |
|---|---|---|---|---|
| Time (hours) Sample # | 0 | 2 | 4 | 24 |
| 1 | $7.3 \times 10^5$ | $2.6 \times 10^4$ | $2.5 \times 10^2$ | 0 |
| 2 | $3.3 \times 10^6$ | $2.2 \times 10^4$ | $2.3 \times 10^3$ | 0 |
| 3 | $6.6 \times 10^5$ | $4.5 \times 10^4$ | $1.5 \times 10^4$ | 0 |
| 4 | $2.5 \times 10^4$ | $6.8 \times 10^1$ | $5.0 \times 10^1$ | 0 |
| 5 | $1.7 \times 10^4$ | unable to count | $1.0 \times 10^1$ | 0 |
| 6 | $2.4 \times 10^4$ | $1.3 \times 10^2$ | $6.5 \times 10^1$ | 0 |

All formulations were effective and a 6 log kill was obtained by 24 hours.

EXAMPLE 2

A formulation was prepared by dry mixing 4.0 grams Dynasorb® Hydrosafe 85 acrylate superabsorbent polymer, 0.75 gram PVP-I 30/06, 150 mg citric acid, and 200 mg of potassium iodate. A control sample was prepared in the absence of PVP-I. The compositions was tested according to the procedure set forth in Example 1 except that 90 mls of saline was used and 10 mls of the spore inoculated suspension was added so that the total volume before the addition of the formulation was 100 mls rather than 110. (Total percent by weight of the composition in solution=5.1%; the percent by weight of the PVP-I in solution=0.71%).

The ingredients were mixed and gelling took place within one minute. Triplicate grab samples were obtained. The samples treated with the control formulation contained an average of $2.1 \times 10^5$ control CFU/g. The formulation (#1) containing the active agent was tested on two different occasions in triplicate and contained an average of 87 CFU/g after 6 hours. Unexpectedly, the formulation was effective in killing 6 logs of Bacillus subtillis spores within 6 hours. The results are listed in Table 9.

TABLE 9

| | (CFU/g) | | | |
|---|---|---|---|---|
| Time (hours) Sample | 0 | 4 | 6 | 8 |
| control | $1 \times 10^5$ | $1.7 \times 10^5$ | $1.5 \times 10^5$ | $2.1 \times 10^5$ |
| #1 | $2.6 \times 10^4$ | $1.9 \times 10^2$ | 47 | 0 |
| #1 | $3.6 \times 10^4$ | $1.4 \times 10^2$ | 87 | 0 |

As seen in Table 9, a substantial bacterial kill was obtained by 6 hours.

EXAMPLE 3

In order to determine the efficacy of test gel powders containing PVP-iodine in contaminated biological materials in a laboratory model system, Pseudomonas_aeruginosa was grown on Tryptic Soy Agar (TSA) media. The organism was then added to sterile 0.85% saline. The concentration of the suspension was approximately $10^9$ CFU/g (colony forming units/g) as determined by a plate-count methodology.

For each sample tested, 25 mls of whole defibrinated sheep blood, 65 mls sterile 0.85% saline solution and 10 mls of the inocula preparation were placed into a specimen container. Test formulations were added to two of these containers, swirled and let sit for two minutes. After predetermined time intervals, quadruplicate grab samples from each container were drawn. One 1 g sample was placed into a petri dish. Three 1 g samples were transferred to tubes each containing 9 mls Neutralizer Broth (Difco) to neutralize the effect of active ingredients.

The Neutralizer Broth-Tubes were serially diluted in Phosphate Buffer Saline (PBS) and then plated in duplicate on TSA. The plates were incubated at 37° C. for 48 hours and the colonies were counted.

Formulations included various levels of PVP-iodine 30/06, an acrylic gelling agent, potassium iodate and acids such as phosphoric acid, citric acid, or boric acid.

Formulations were prepared as listed in Table 10–12.

TABLE 10

PVP-I GEL FORMULATIONS TESTED IN BLOOD/SALINE (25%/75%)

| Formulation Number | Medi-Gel ® 100 superabsorbent polymer (% solution) | PVP-I 30/60 (% in solution) | Potassium iodate (% in solution) | Total Weight in Solution (%) |
|---|---|---|---|---|
| 1 | 2.7 | 0.3 | | 3.0 |
| 2 | | 9.0 | 0.5 | 9.5 |
| 3 | | 9.0 | 0.05 | 9.05 |
| 4 | 2.7 | 8.8 | 0.04 | 11.5 |
| 5 | 2.9 | 1.0 | 0.05 | 4.0 |

TABLE 11

PVP-I GEL FORMULATIONS TESTED IN BLOOD/SALINE (25%/75%)

| Formulation Number | Medi-Gel ® 100 superabsorbent polymer (% solution) | PVP-I 30/60 (% in solution) | Potassium iodate (% in solution) | Total Weight in Solution (%) |
|---|---|---|---|---|
| 6(2d) | 2.9 | 1.0 | 0.05 | 4.0 |
| 7 | 2.9 | 1.0 | 0.05 | 4.0 |
| 8 | 1.9 | 0.9 | 0.05 | 2.9 |
| 9 | 2.9 | 1.0 | 0.05 | 4.0 |
| 10 | 2.9 | 1.0 | 0.19 | 4.0 |
| 11 | 2.9 | 1.0 | 0.05 | 4.0 |
| 12 | 2.9 | 1.0 | 0.19 | 4.0 |
| 13 | 2.9 | 1.0 | 0.05 | 4.0 |

TABLE 12

PVP-I GEL FORMULATIONS TESTED IN BLOOD/SALINE (25%/75%)

| Formulation Number | Medi-Gel ® 100 superabsorbent polymer (% solution) | PVP-I 10/26 (% in solution) | Potassium iodate (% in solution) | Acid (% in solution) | Total Weight in Solution (%) |
|---|---|---|---|---|---|
| 14 (19) | 2.9 | 1.0 | 0.05 | | 4.0 |
| 15 (20) | 2.9 | 1.0 | 0.05 | | 4.0 |
| 16 (21) | 2.9 | 1.0 | 0.05 | 0.10 phosphoric | 4.0 |
| 17 (22) | 1.5 | 1.0 | 0.10 | 0.10 boric | 2.6 |
| 18 (23) | 1.5 | 0.73 | 0.10 | 0.10 boric | 2.4 |
| 19 (24) | 1.5 | 1.0 | 0.10 | 0.10 | 2.6 |
| 20 (26) | 2.9 | 1.0 | 0.19 | | 4.0 |

Formulations #1, #3 and Isolyzer LTS 2000 was tested in 90/10% defibrinated sheep blood/saline and no formulation was capable of disinfecting solutions with such a high blood load.

TABLE 13

NUMBER OF BACTERIA KILLED (CFU/G IN LOG UNITS)

| Formulation | 0 min. | 15 min. | 30 min. | 45 min. | 1 Hour | 2 Hours | 4 Hours | 6 Hours | 24 Hours |
|---|---|---|---|---|---|---|---|---|---|
| 1 | 2 | 2 | 2 | <5 | <5 | | | | <3 |
| 2 | 2 | 2 | 2 | 2 | 2 | | | | <3 |
| 3 | 0 | 1 | 1 | 1 | 2 | | | | |
| 6 | 2 | 1 | 2 | 2 | 2 | | | | 9 |
| 7 | 9 | | | | | | | | 9 |
| 8 | 9 | | | | | | | | 9 |
| 9 | 8 | 9 | | | | | | | 9 |
| 10 | 1 | 1 | 2 | 2 | 21 | | | | 2 |
| 11A | 2 | 2 | 3 | 3 | 3 | | | | 9 |
| 12 | 2 | | | | 2 | <3 | <6 | <6 | 6 |
| 13 | 2 | | | | 3 | 4 | 5 | 5 | 4 |
| 11B | 3 | | | | 4 | 4 | 5 | 5 | 9 |
| 14 | 3 | | | | 5 | 6 | 7 | 7 | 9 |
| 15 | 3 | | | | 6 | 8 | 9 | 9 | 9 |
| 16 | 7 | | | | 7 | 7 | 7 | 6 | 5 |
| 17 | 7 | | | | 6 | 4 | 3 | 3 | |
| 18 | 7 | | | | 7 | 7 | 6 | 6 | |
| 19 | | | | | 8 | 7 | | | 6 |
| 20 | 5 | | | | 5 | 5 | 4 | 4 | 2 |

Isolyzer LTS 2000 was tested in 25% whole defibrinated sheep blood and 75% saline solution. At one hour, a kill rate of two logs was achieved and at 24 hours, a four log kill rate was achieved. Formulations #2–4 resulted in immediate high kill rates but contained excessively high PVP-iodine levels.

Formulations #5–20 involved similar ingredients but at different levels. Formulation #10 shows that increasing the level of potassium iodate from 0.01% to 0.03% (on a dry blend basis) results in moderately improved results.

The results indicate that a six log kill rate is achievable within one hour (e.g., Formulation #10). Within six hours, several formulations achieved this desired kill rate.

The results indicate that cost effective and fast acting disinfecting gelling formulations can be achieved by combining PVP-I with a gelling agent.

The invention has been described with reference to various specific embodiments. However, many variations and modifications may be made while remaining within the scope and spirit of the invention.

What is claimed is:

1. A method of treating liquid waste comprising: adding polyvinylpyrrolidone, iodine, and a gelling agent to an aqueous waste stream such that the concentration of the combined weight of the polyvinylpyrrolidone and iodine is greater than 0.3%, by weight, of the total weight of the waste, polyvinylpyrrolidone, iodine and gelling agent.

2. The method as recited in claim 1 further comprising adding an iodate salt.

3. The method as recited in claim 1 wherein the gelling agent is a polyacrylate.

4. The method as recited in claim 2 wherein the gelling agent is a polyacrylate.

5. The method as recited in claim 1 wherein the weight of the combined weight of the polyvinylpyrrolidone and the iodine composition is, when less than 10 grams of the composition is added to 90 grams of a liquid waste containing blood, from about 0.4 to 0.5% to about 0.7 to 0.8% of the total weight of the waste containing the composition.

6. The method as recited in claim 2 wherein the weight of the combined weight of the polyvinylpyrrolidone and the iodine composition is, when less than 10 grams of the composition is added to 90 grams of a liquid waste containing blood, from about 0.4 to 0.5% to about 0.7 to 0.8% of the total weight of the waste containing the composition.

7. The method as recited in claim 3 wherein the weight of the combined weight of the polyvinylpyrrolidone and the iodine composition is, when less than 10 grams of the composition is added to 90 grams of a liquid waste containing blood, from about 0.4 to 0.5% to about 0.7 to 0.8% of the total weight of the waste containing the composition.

8. The method as recited in claim 4 wherein the weight of the combined weight of the polyvinylpyrrolidone and the iodine composition is, when less than 10 grams of the composition is added to 90 grams of a liquid waste containing blood, from about 0.4 to 0.5% to about 0.7 to 0.8% of the total weight of the waste containing the composition.

9. The method as recited in claim 1 wherein the weight of the combined weight of the polyvinylpyrrolidone and the iodine composition is, when less than 10 grams of the composition is added to 90 grams of a liquid waste containing blood, from about 0.3 to about 1% of the total weight of the waste containing the composition.

10. The method as recited in claim 2 wherein the weight of the combined weight of the polyvinylpyrrolidone and the iodine composition is, when less than 10 grams of the composition is added to 90 grams of a liquid waste containing blood, from about 0.3 to about 1% of the total weight of the waste containing the composition.

11. The method as recited in claim 3 wherein the weight of the combined weight of the polyvinylpyrrolidone and the iodine composition is, when less than 10 grams of the composition is added to 90 grams of a liquid waste containing blood, from about 0.3 to about 1% of the total weight of the waste containing the composition.

12. The method as recited in claim 4 wherein the weight of the combined weight of the polyvinylpyrrolidone and the iodine composition is, when less than 10 grams of the composition is added to 90 grams of a liquid waste containing blood, from about 0.3% to about 1% of the total weight of the waste containing the composition.

13. A system for treating liquid waste stream comprising:

(a) an aqueous waste comprising human liquid waste;

(b) a polyvinylpyrrolidone and iodine complex wherein the concentration of the complex is, by weight of the total weight of the system, greater than 0.3%; and (c) a gelling agent.

* * * * *